US00PP08502P

United States Patent [19]

Jessel, Jr.

[11] Patent Number: Plant 8,502

[45] Date of Patent: Dec. 14, 1993

[54] CARNATION PLANT NAMED CFPC PINK SATIN

[75] Inventor: Walter H. Jessel, Jr., Salinas, Calif.

[73] Assignee: California Florida Plant Co., L.P., Salinas, Calif.

[21] Appl. No.: 950,305

[22] Filed: Sep. 24, 1992

[51] Int. Cl.[5] ..... A01H 5/00

[52] U.S. Cl. ..... Plt./70.5

[58] Field of Search ..... Plt./70.5, 70.6, 70.1

*Primary Examiner*—Howard J. Locker

*Attorney, Agent, or Firm*—Christie, Parker & Hale

[57] ABSTRACT

A new carnation of clear light pink coloration.

1 Drawing Sheet

SUMMARY OF THE INVENTION

The present invention relates to a new and distinct variety of carnation plant which was originated by me in a controlled breeding program by my crossing as seed and pollen parents, two unnamed and unpatented seedlings of my creation. The varietal denomination of this new carnation is 'CFPC Pink Satin'.

Among the novel combination of characteristics possessed by the new variety which distinguishes it are flowers of the attractive light pink flower coloring which resist fading on fast flowering response of 3½ to 4 months.

'CFPC Pink Satin' differs from 'Londaison', U.S. Plant Pat. No. 5,789, which exhibits severe fading of the petal margins and a grassy overproductive plant habit. The new variety resists fading and is usually the first light pink of commercial varieties to flower.

Asexual reproduction by propagation by side shoot cuttings of the new variety as performed in Salinas, Calif., shows that the foregoing and other distinguishing characteristics come true to form and are established and transmitted through succeeding propagations. Although propagation by side shoot cuttings is described, other known methods of asexual reproduction may also be used to reproduce 'CFPC Pink Satin'.

BRIEF DESCRIPTION OF THE ILLUSTRATION

The accompanying illustration shows typical specimens of the vegetative growth and flowers in different stages of development of the new variety depicted in color as nearly true as it is reasonably possible to make the same in a color illustration of this character. Although propagation by side shoot cuttings is described, other known methods of asexual reproduction may also be used to reproduce 'CFPC Pink Satin'.

DESCRIPTION OF THE NEW VARIETY

The following is a detailed description of my new variety, with color terminology in accordance with The Royal Horticultural Society Color Chart (RHSCC). The terminology used in the color description herein refers to plate numbers in the aforementioned color chart. Color designations and color descriptions may deviate from the stated values depending upon varying environmental, seasonal and cultural conditions.

The information provided herein is based on observations of plants grown inside commercial greenhouses at Fremont, Calif. The height of plant and flower and foliage size are established as an average using standard commercial cultural practices.

Name: 'CFPC Pink Satin'.

Classification:

*Botanical.*—*Dianthus caryophyllus.*

*Commercial.*—Carnation, spray type.

Parentage:

*Female parent.*—Unnamed seedling (No. 870775).

*Male parent.*—Unnamed seedling (No. 871000).

PLANT

Height: About 29 inches.
Growing habit: Herbaceous, semi-upright.
Blooming habit: Terminal as a spray.
Blooming season: Year round.
Rooting time: About 14 days.
Mutation prone: Does not appear to be.
Disease resistance: Good.
Temperature tolerance: Typical for carnation.
Breaking action: Good.

FOLIAGE

Color:

*Upper side.*—Near 135A.

*Lower side.*—Near 139A.

Size: About 6½ inches long at base of plant.
Quantity: Numerous.
Shape: Lanceolate.
Texture: Smooh.
Ribs: Central, keeled.
Arrangement: Bi-lateral along stem.
Stem Color: Green.

BUD

Shape: Oval.
Color: Green.
Length: About 1½ inches.
Diameter: About ½-inch.

CALYX

Number of sepals: About 5.
Length: About 1-inch.
Width: About ½-inch.
Color:

*Outside.*—Near 143B.

*Inside.*—Near 142C.

BLOOM

Shape: Round.

Size:

*Diameter average.*—About 2⅓ inches.

*Depth average.*—About 1½ inches.

Borne: Terminal as a spray.

Color:

*General tonality.*—Light pink.

*Upper side.*—Near to from 38C to 36D.

*Lower side.*—Near 36D.

*Center.*—Near 38C.

*Outer petals.*—Near to from 38C to 36D.

Keeping quality: Very good.

Fragrance: Slight.

PETALS

Number: About 50.

Outer petals:

*Length.*—About 1½ inches.

*Width.*—About 1-inch.

Central Petals:

*Length.*—About 1-inch.

*Width.*—About ¼-inch.

Texture: Smooth.

Form: Fan shaped.

Appearance: Shiny.

REPRODUCTIVE ORGANS

Stamens:

*Number.*—About 16.

*Arrangement.*—Around the ovary.

Anthers:

*Length.*—About ⅛ inch.

*Color.*—Near 157A.

Filaments:

*Length.*'About 1¼ inches.

*Color.*—Near 157D.

Pistil:

*Number.*—About 2.

*Color.*—Near 157D.

Stigma:

*Number.*—About 2.

*Color.*—Near 157D.

Ovary:

*Shape.*—Conical.

*Color.*—Base — green. Body — green. Apex — tan.

Fertility:

*Male.*—Poor.

*Female.*—Good.

I claim:

1. A new and distinct variety of carnation plant, substantially as shown and described.

* * * * *

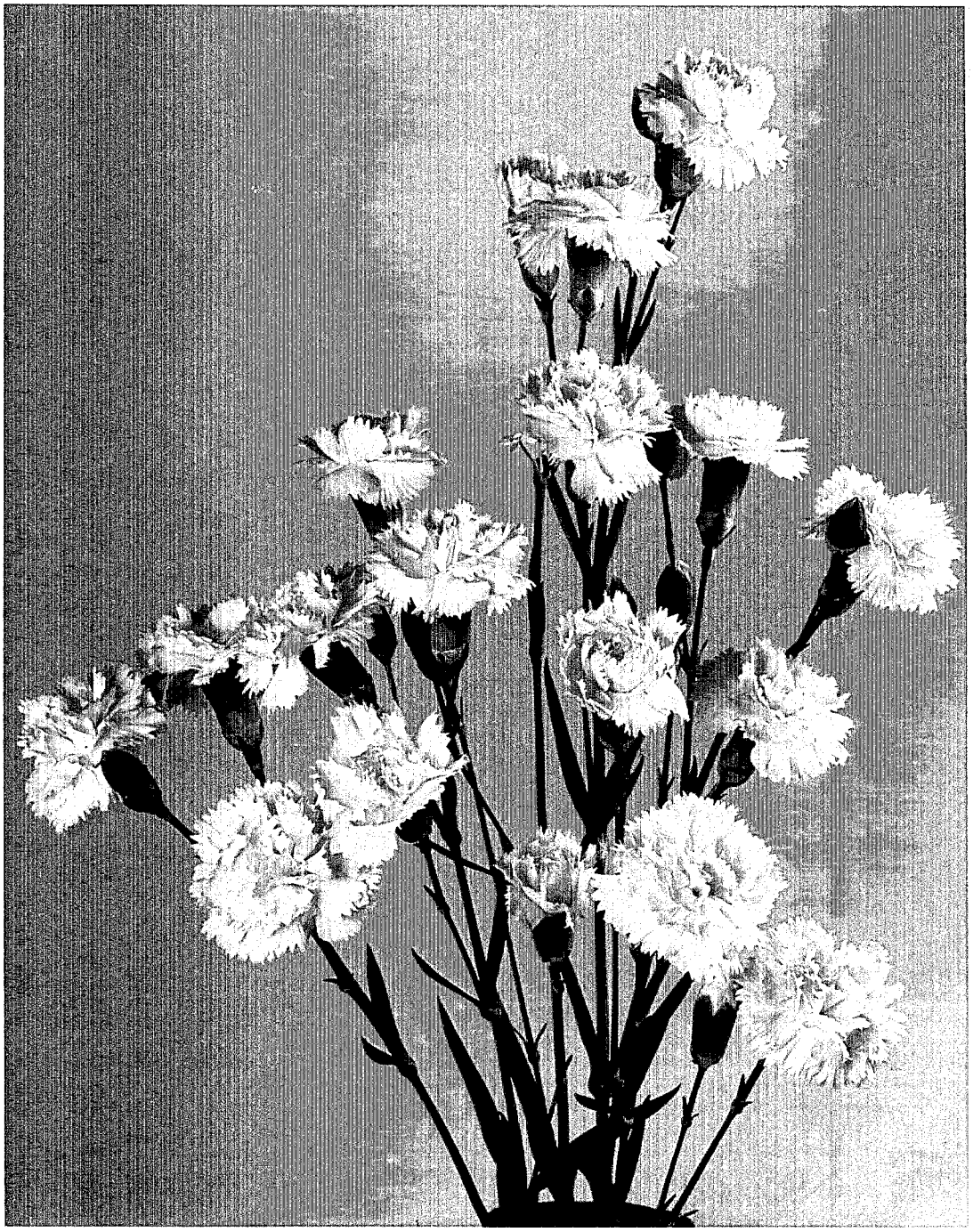

UNITED STATES PATENT AND TRADEMARK OFFICE

CERTIFICATE OF CORRECTION

PATENT NO. : Plant 8,502

DATED : December 14, 1993

INVENTOR(S) : Walter H. Jessel, Jr.

It is certified that error appears in the above-indentified patent and that said Letters Patent is hereby corrected as shown below:

Column 1, lines 34-37, delete the following sentence:

"Although propagation by side shoot cuttings is described, other known methods of asexual reproduction may also be used to reproduce 'CFPC Pink Satin'."

Column 2, line 30, change "Smooh" to -- Smooth --.

Column 4, line 10, change "Length.'" to -- Length: --.

Signed and Sealed this

Twenty-first Day of June, 1994

*Attest:*

Bruce Lehman

BRUCE LEHMAN

*Attesting Officer*

*Commissioner of Patents and Trademarks*